(12) United States Patent
Slepian

(10) Patent No.: US 11,298,290 B2
(45) Date of Patent: Apr. 12, 2022

(54) SYSTEMS, DEVICES, AND METHODS FOR MONITORING AND MODULATION OF THERAPEUTIC PROCEDURES

(71) Applicant: Arizona Board of Regents on Behalf of the University of Arizona, Tucson, AZ (US)

(72) Inventor: Marvin J. Slepian, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 227 days.

(21) Appl. No.: 16/492,583

(22) PCT Filed: Mar. 9, 2018

(86) PCT No.: PCT/US2018/021883
§ 371 (c)(1),
(2) Date: Sep. 9, 2019

(87) PCT Pub. No.: WO2018/165634
PCT Pub. Date: Sep. 13, 2018

(65) Prior Publication Data
US 2021/0137780 A1    May 13, 2021

Related U.S. Application Data

(60) Provisional application No. 62/469,503, filed on Mar. 9, 2017.

(51) Int. Cl.
*A61H 31/00* (2006.01)
*G16H 20/30* (2018.01)
(Continued)

(52) U.S. Cl.
CPC ........... *A61H 31/005* (2013.01); *A61H 99/00* (2013.01); *G09B 19/003* (2013.01); *G16H 20/30* (2018.01);
(Continued)

(58) Field of Classification Search
CPC ...... A61H 31/00; A61H 31/005; A61H 99/00; A61H 2201/501; A61H 2201/5043;
(Continued)

(56) References Cited

U.S. PATENT DOCUMENTS

| 9,028,407 B1 | 5/2015 | Bennett-Guerrero |
| RE45,922 E | 3/2016 | Marcovecchio et al. |

(Continued)

OTHER PUBLICATIONS

International Search Report and Written Opinion of PCT/US2018/021883 dated May 21, 2018, 12 pp.

*Primary Examiner* — Timothy A Musselman
(74) *Attorney, Agent, or Firm* — Lathrop GPM LLP

(57) ABSTRACT

Wearable sensors that measure one or more parameters such as pressure, force, acceleration, or skin temperature, are used to measure, record, display and monitor the efficacy of therapeutic maneuvers applied to a subject by an operator. Systems and methods for assessing the physiological efficacy of therapeutic maneuvers performed by an operator on a subject in need thereof, and provide a way to guide subsequent therapeutic maneuvers toward optimal outcome. In some embodiments, the systems and methods measure, record, and display physiological parameters of an operator and/or subject during application of cardiopulmonary resuscitation (CPR).

26 Claims, 12 Drawing Sheets

(51) Int. Cl.
*G16H 40/67* (2018.01)
*A61H 99/00* (2006.01)
*G09B 19/00* (2006.01)

(52) U.S. Cl.
CPC ....... *G16H 40/67* (2018.01); *A61H 2201/501* (2013.01); *A61H 2201/5043* (2013.01); *A61H 2201/5061* (2013.01); *A61H 2201/5071* (2013.01); *A61H 2201/5079* (2013.01); *A61H 2201/5084* (2013.01); *A61H 2201/5092* (2013.01); *A61H 2230/04* (2013.01); *A61H 2230/207* (2013.01); *A61H 2230/40* (2013.01); *A61H 2230/50* (2013.01)

(58) Field of Classification Search
CPC .... A61H 2201/5061; A61H 2201/5071; A61H 2201/5079; A61H 2201/5084; A61H 2201/5092; A61H 2230/04; A61H 2230/207; A61H 2230/40; A61H 2230/50; G16H 20/30; G09B 19/00; G09B 19/003
See application file for complete search history.

(56) References Cited

U.S. PATENT DOCUMENTS

| | | | |
|---|---|---|---|
| 10,426,695 B2 * | 10/2019 | Addison | A61B 5/0205 |
| 2003/0233129 A1 | 12/2003 | Matos | |
| 2007/0043585 A1 | 2/2007 | Matos | |
| 2010/0022886 A1 | 1/2010 | Ayati et al. | |
| 2012/0089054 A1 | 4/2012 | Centen et al. | |
| 2013/0218057 A1 | 8/2013 | Jorgenson et al. | |
| 2014/0135666 A1 | 5/2014 | Butler et al. | |
| 2015/0265845 A1 * | 9/2015 | Sullivan | A61N 1/3968 607/8 |
| 2016/0278652 A1 | 9/2016 | Kaib et al. | |
| 2017/0273864 A1 * | 9/2017 | Kaufman | A61H 31/005 |
| 2017/0368413 A1 * | 12/2017 | Shavit | G06K 9/00342 |
| 2018/0102190 A1 * | 4/2018 | Hogue | G16H 20/40 |

\* cited by examiner

FORCE DATA OF TRAINED INDIVIDUAL PERFORMING CPR

FORCE DATA OF UNTRAINED INDIVIDUAL PERFORMING CPR

SYSTEMS, DEVICES, AND METHODS FOR MONITORING AND MODULATION OF THERAPEUTIC PROCEDURES

PRIORITY CLAIM

The present application is a 35 U.S.C. 371 national phase entry of, and claims priority from, Patent Cooperation Treaty patent application PCT/US2018/021883, filed 9 Mar. 2018. In turn, PCT US/2018/021883 claims priority from U.S. Provisional Patent Application 62/469,503 filed 9 Mar. 2017. The entirety of the aforementioned Patent Applications are incorporated herein by reference.

FIELD

The invention relates to systems and methods for measuring, recording and displaying therapeutic maneuvers applied to a patient, and providing feedback information relating to efficacy and therapeutic effect in real time.

BACKGROUND

There is lack of consistency in the way that hospital workers, care givers, and average people administer and provide therapeutic maneuvers to patients. In particular, the method and efficacy of Cardiopulmonary Resuscitation (CPR) technique varies widely amongst caregivers. Although methods of administering CPR have changed over time, with current CPR emphasizing compression only, versus a combination of intermittent compression and ventilation as was taught in the past, the way in which CPR is taught, monitored, and quantified have changed very little. While standards and guidelines for CPR exist and are continually updated (see 1. Circulation. 2010;122:S640-S656; Circulation. 2010;122:S720-S728; Circulation. 2017; 136:e424-e440) medical care providers, and the general public, presently in real-world practice rely on subjective measures, or "how the procedure feels," to determine whether variables including frequency, force, and pressure, are being administered adequately and correctly to provide optimal effect to the patient. There is currently no standardized method to quantitate motion, force or similar variables and parameters, or to improve quality and quantity or impact of the motion and procedural components. In some instances, measurements of movement are recorded using cameras to record the CPR process, but evaluating these measurements is impractical, cannot be done in the field or setup instantaneously or contemporaneous to a sudden cardiac arrest event, are inaccurate, and are highly subjective.

SUMMARY

There remains need for methods, devices and systems to determine whether manipulation of a subject is carried out correctly, or to provide the greatest chance of successful intervention.

We provide systems to record and quantitate the maneuvers associated with cardiopulmonary resuscitation (CPR) technique and similar manipulative procedures effectuated on a patient—e.g. Heimlich maneuver. We also provide methods of recording and reproducing a motion signature associated with a therapeutic maneuver. We also provide methods of creating an organized network of data from multiple patients over time allowing for machine learning to be applied to identify optimized performance as relates to survival and similar outcome variables.

The present system and methods provide for assessing the functional and physiological efficacy of therapeutic maneuvers performed by an operator or a device on a subject in need thereof, and providing means to guide subsequent therapeutic maneuvers toward optimal outcome.

Wearable sensors that measure movement, displacement, pressure, force, acceleration, temperature, etc. can measure, record, display, analyze and monitor efficacy of therapeutic maneuvers applied to a subject by an operator.

Systems and methods for measuring, recording, analyzing and displaying physiological parameters of a subject during application of therapeutic maneuvers like cardiopulmonary resuscitation (CPR) are provided.

In an embodiment, a system adapted to monitor cardiopulmonary resuscitation (CPR), including at least one three-dimensional (3D) measurement gauge, sensor or system—which can include an accelerometer gyroscope, strain gauge or similar measurement system, the measurement gauge, sensor or system (3D accelerometer) configured for attachment to the center of a sternum of a subject, the measurement gauge, sensor or system comprising digital capabilities for data storage and telemetry—e.g. a radio adapted to link to a master short range digital radio, near field, Bluetooth or other telecommunication protocol and means. The system also includes an analysis and display unit including the master short-range digital radio, a processor, a memory, a signature database stored within the memory further comprising at least one signature corresponding to a prior CPR session, and code including machine readable instructions configured to direct the processor to read gauge, sensor or system —i.e. accelerometer data through the short range digital radio from the accelerometer, to determine vertical and lateral movements of the subject's chest from the accelerometer data, and to determine and display parameters derived from the movements of the subject's chest including depth and rate of CPR compressions, and to compare a signature derived from a present CPR session to the at least one signature corresponding to a prior or ideal CPR session.

In an embodiment, a system adapted to monitor cardiopulmonary resuscitation (CPR), including at least one three-dimensional (3D) accelerometer, the 3D accelerometer selected from a 3D accelerometer configured for attachment to a center of a sternum of a subject and a pair or network of 3D accelerometers including a 3D accelerometer configured for attachment over a sternal notch of a subject and a 3D accelerometer configured for attachment over a xiphoid process of the subject, the 3D accelerometers comprising a digital radio adapted to link to a master short range digital radio. The system also includes an analysis and display unit including the master short-range digital radio, a processor, a memory, a signature database stored within the memory further comprising at least one signature corresponding to a prior CPR session, and code including machine readable instructions configured to direct the processor to read accelerometer data through the short range digital radio from the accelerometers, to determine vertical and lateral movements of the subject's chest from the accelerometer data, and to determine and display parameters derived from the movements of the subject's chest including depth and rate of CPR compressions, and to compare a signature derived from a present CPR session to the at least one signature corresponding to a prior or ideal CPR session.

In another embodiment, a method, over a short range digital radio link, sensor data including accelerometer data from at least one three-dimensional accelerometer configured for attachment to a subject, the accelerometer data indicative of accelerations of a sternum of the subject; and determining vertical and lateral movements of the subject's chest from the accelerometer data, and displaying parameters derived from the movements of the subject's chest including depth and rate of CPR compressions and lateral motions.

DETAILED DESCRIPTION OF THE EMBODIMENTS

Wearable sensors can be used to measure and quantitate application of motion and force to a patient to manipulate the patient during a medical procedure. Sensors can also be employed to measure one or more additional physiological parameters of a subject, such as body temperature, oxygen level, pulse rate, blood flow, respiratory rate, sweat production etc.

Figure 1A:
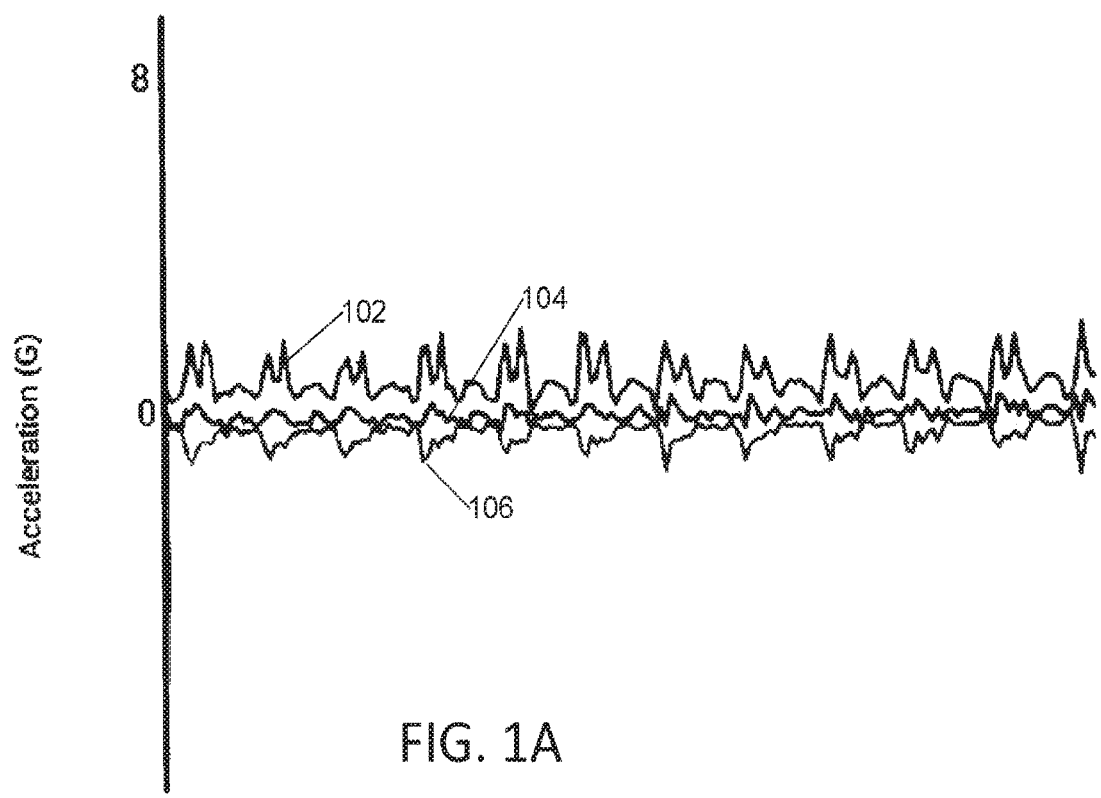
FIG. 1A-1E are graphs showing motion traces recorded by a motion sensor, showing acceleration (Gravities) over time (seconds) for motion in each of three planes, X, Y and Z, respectively; some of these motion traces are from CPR performed by experienced ACLS-certified operators, while those depicted in FIGS. 1B, 1D and 1E are produced by less-experienced operators and may betray poor CPR performance despite the operators involved possible belief they were providing good CPR.
Figure 1C:
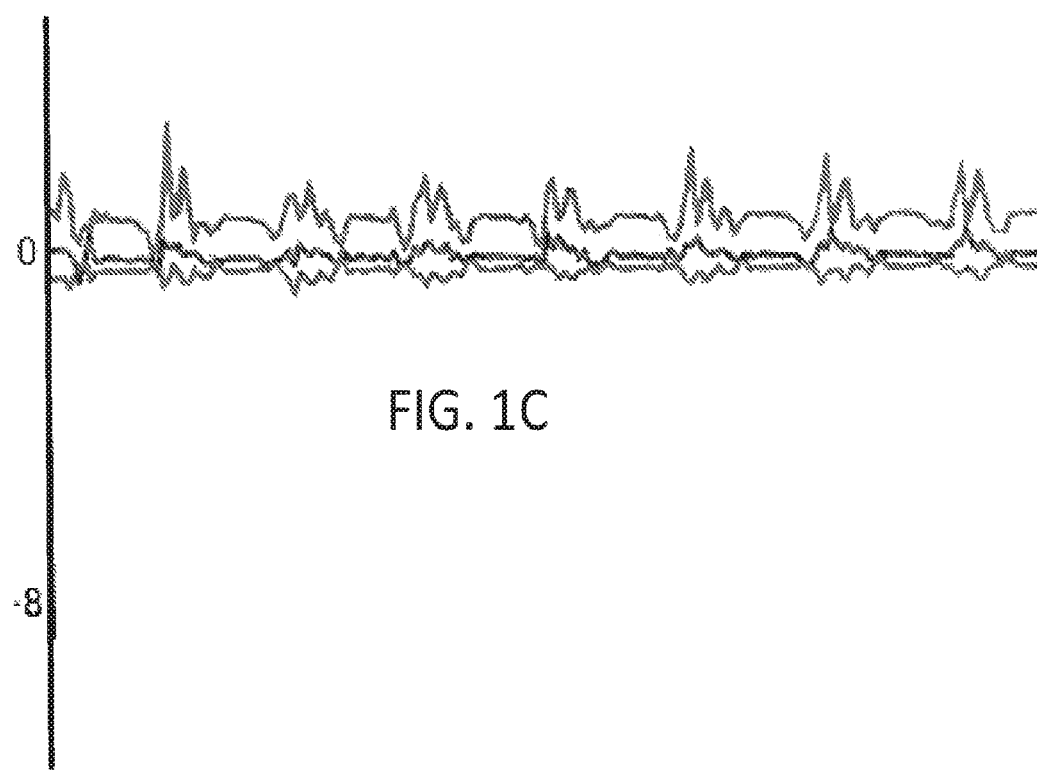
Figure 1B:
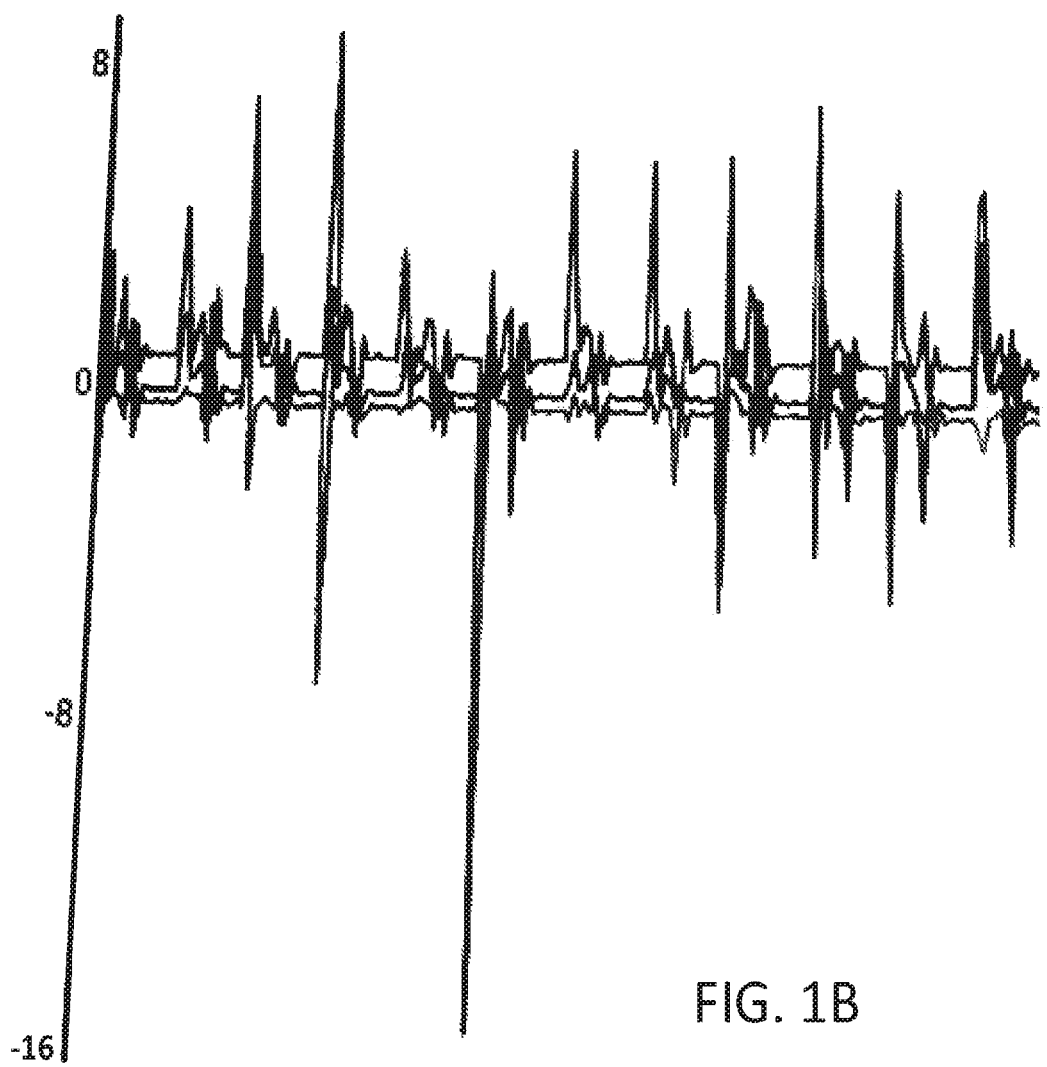
Figure 1D:
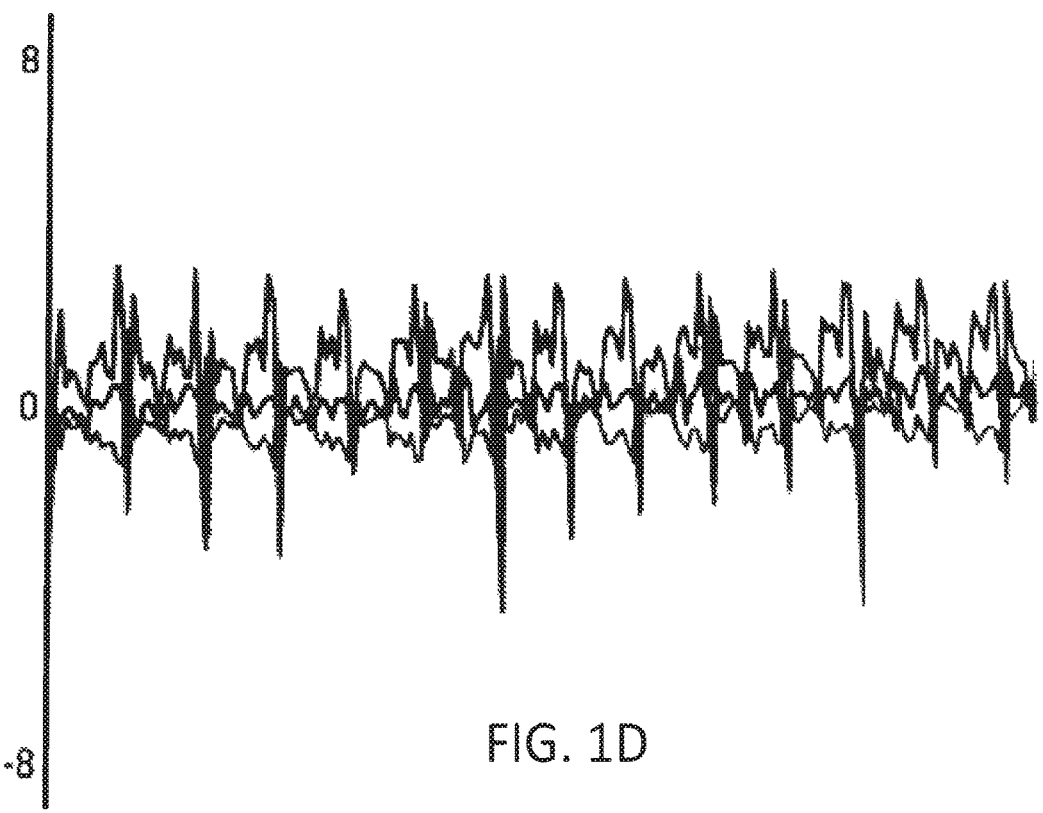
Figure 1E:
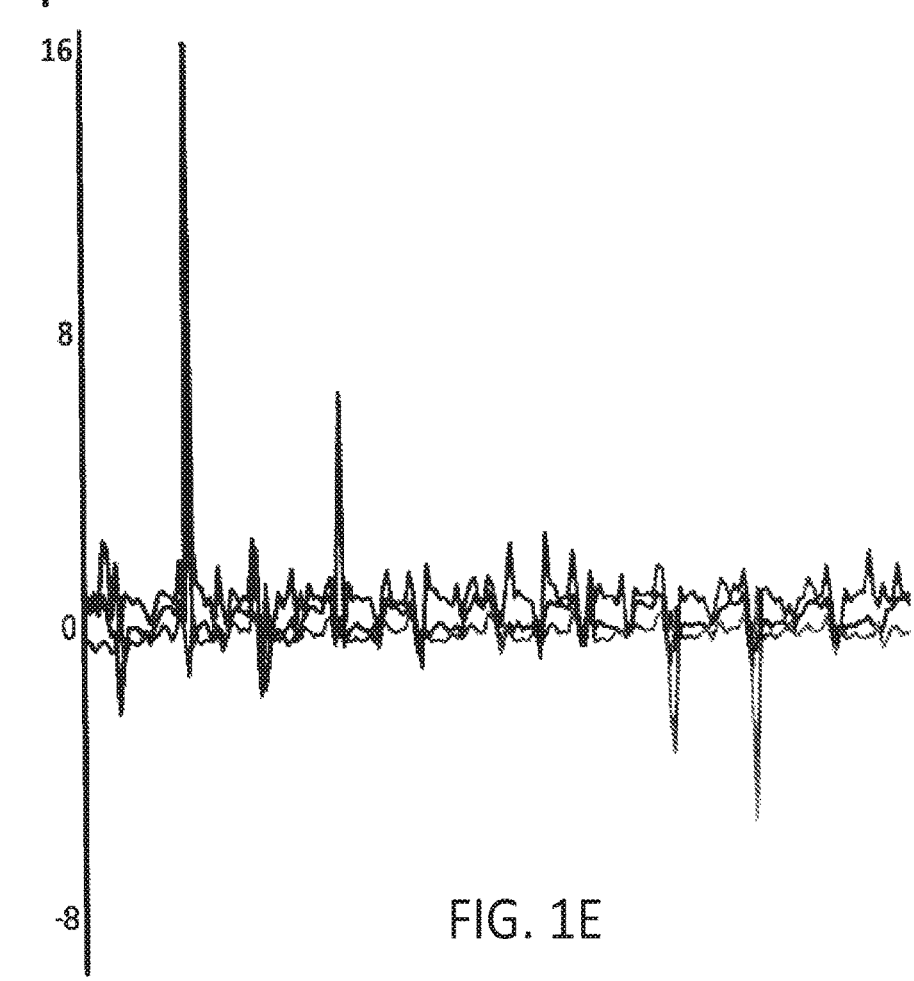
Figure 1F:
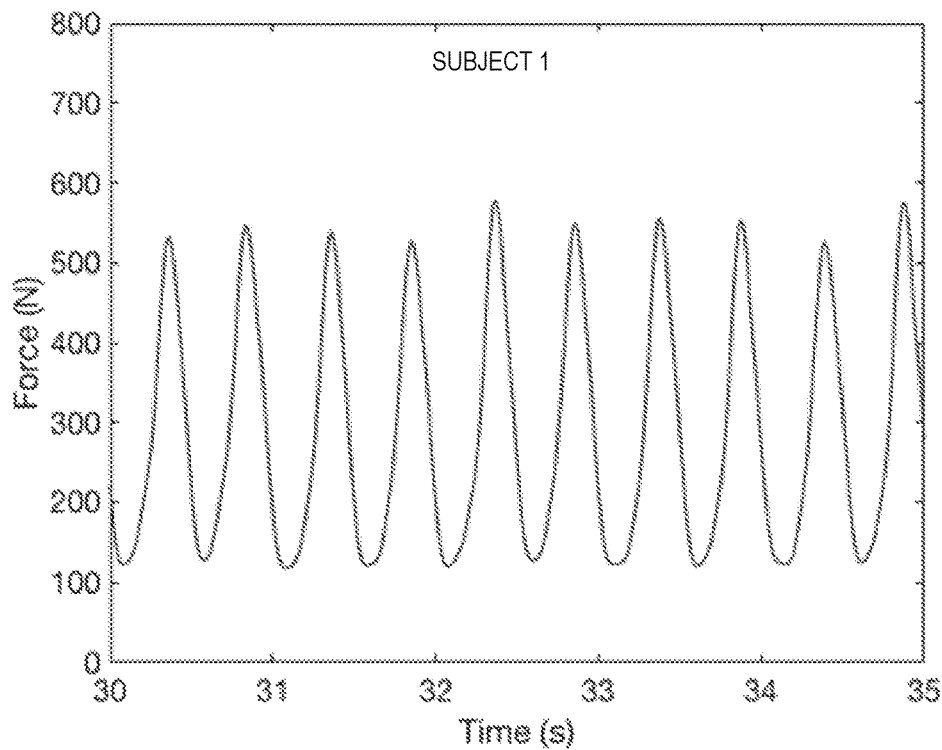
FIGS. 1F and 1G are graphs showing example force data of a trained individual applying CPR to two different subjects.
Figure 1G:
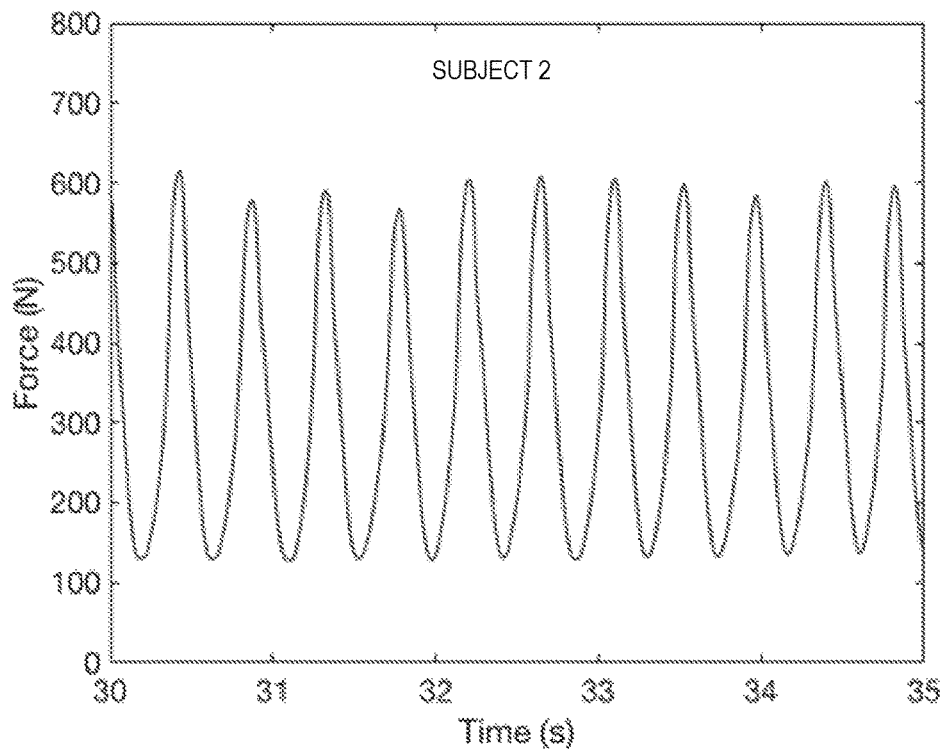

FIGS. 1F and 1G are graphs showing example force data of a trained individual applying CPR to two different subjects. As shown, the trained individual applies forces consistently to each subject, with a peak strength between 500 and 600 Newton, and a depth of around 400 Newton. It is clear that the trained individual generates consistent forces that are quantitatively detectable, with identifiable intensity, periodicity, frequency and fidelity from captured signals.

Figure 1H:
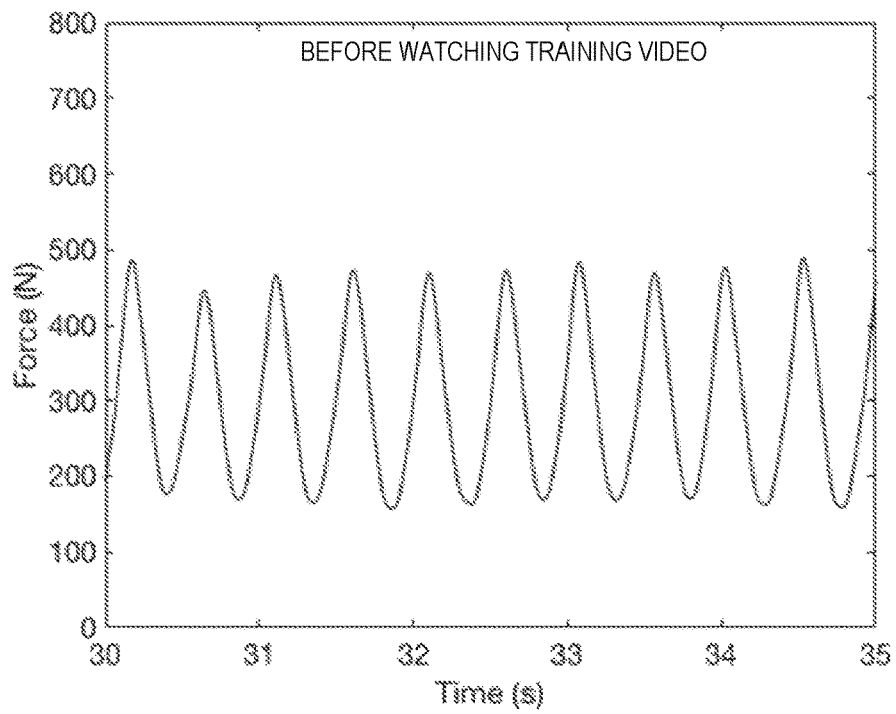
FIGS. 1H and 1I are graphs showing example force data of an untrained individual applying CPR.
Figure 1I:
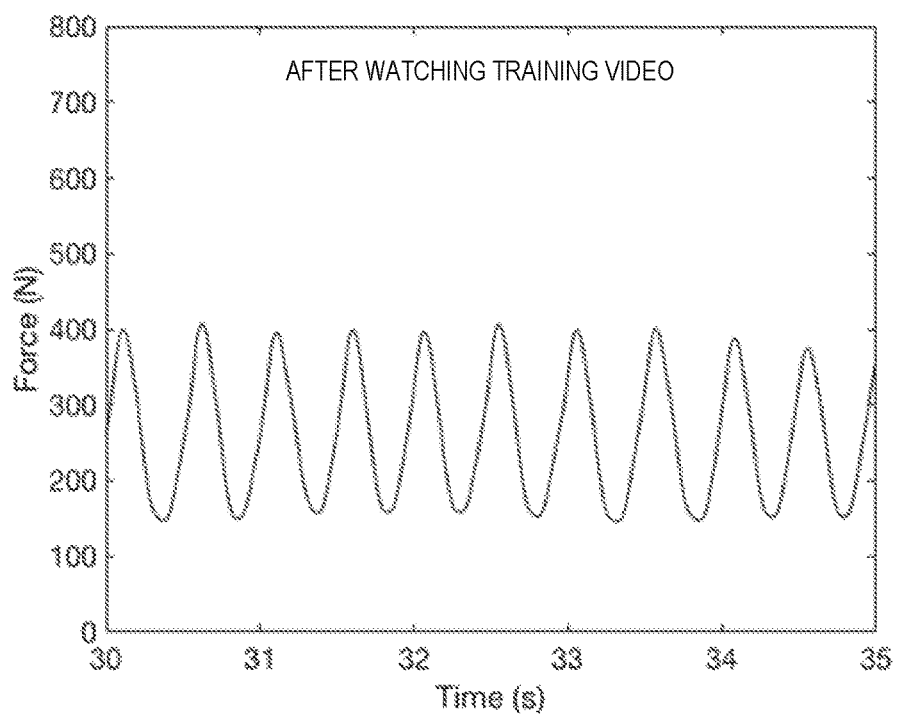

FIGS. 1H and 1I are graphs showing example force data of an untrained individual applying CPR. It should be noted that the untrained individual believed they were applying CPR correctly, and may have appeared visually to be doing so. Particularly, FIG. 1H shows sensed forces applied by the untrained individual before watching a training video, and FIG. 1I shows sensed forces of the untrained individual after watching the trained video. However, in comparison to forces generated by the trained individual, as shown in FIGS. 1F and 1G, it is clear that the untrained individual generates much less force, peaking between 400 and 500 Newton, and with a depth of 300 Newton or less. Interestingly, despite watching a training video, the subsequent performance of the untrained individual, as shown by FIG. 1I, is actually worse than their performance before watching the video.

It is thus very clear from this captured data that real-time monitoring of forces, accelerations, etc., is needed to quantify CPR movements, and that individuals would benefit from real-time feedback of that performance to learn whether the forces and movements they are applying are successfully administering CPR, and thereby learn to adjust their performance to correctly apply CPR.

The systems described herein may be deployed within hospitals, airports, on ambulances and fire-rescue trucks, sports stadiums and other large venues, and in other locations including "heartsafe" communities, which are communities with either aware, trained or networked residents or affiliated individuals, as to health and disease and urgencies of response to acute decompensation.

In certain embodiments, the parameters that are measured and monitored by wearable sensors include the rate of compression, depth of compression, regularity of compression, magnitude and consistency of force applied to a subject's chest, pressure applied and generated, recoil force during CPR.

In certain embodiments, the parameters that are measured and monitored by wearable sensors include the movements of compressive elements—hands, forearms, arms, torso by the performer of CPR—either man or machine, during CPR.

In other embodiments the parameters that are measured and monitored are the outcomes and effects of maneuvers applied by the performer of the maneuver—man or machine, to a patient, for example, during CPR or after manipulating a patient's body during rehabilitation procedures.

I. Systems

Systems for quantitating motion and/or physiological parameters of a subject are provided. The systems include (1) sensors to quantitate and monitor a therapeutic maneuver applied to a subject, such as CPR compression, physiotherapy of a limb, physiotherapy of the torso, physiotherapy of the head and/or neck, ventilation, intubation, or any other manipulation or compression, of a body part; and (2) means to display the quantitated data.

These systems include sensors and processing hardware that quantitates and displays data relating to multiple physiological parameters during a therapeutic procedure. The sensors quantitate motion and other parameters, with multiple degrees of freedom, and enable response from an operator within a closed-feedback loop. The systems include apparatus to measure and quantify parameters including motion, such as coordinate displacement in one or more axes, rate of motion, such as acceleration and deceleration, velocity, displacement, force, pressure, angular displacement, temperature, mass and extension. In certain embodiments, systems measure coordinate displacement in more than a single plane, such as two or three different planes. These systems can measure one or more different parameters simultaneously, or, measure the same or different parameters at different times.

Sensors of the system can be placed on any body part. Typically, the sensors are wearable motion sensors. Wearable sensors can be applied directly to the skin, or placed onto the skin via one or more intermediate layers, such as clothing, hair, bandages, or other sensors. Exemplary sites of application include the chest, the head, the arm, the leg, the torso, the digits, the neck, the wrist, the back, the buttocks, the groin, the hand, the feet, the tongue, lips or scalp.

The systems typically include wearable sensors placed on the subject according to the site of manipulation or as required by the system. In some embodiments, systems include sensors on the subject to whom a therapeutic maneuver is being applied. In other embodiments, systems include sensors on the operator, device or machine, performing a therapeutic maneuver on a subject. In other embodiments, systems acquire and record data from sensors on the operator, device or machine, that is performing a therapeutic maneuver on a subject and sensors on the subject to whom a therapeutic maneuver is being applied.

The systems quantify sensory information during a therapeutic process and can produce an optimized motion signature for the therapeutic process. Typically, the motion signature produced by the system provides a way to determine the quality of the motion as it relates to a desired therapeutic effect. The systems provide feedback enabling a closed-feedback loop to optimize the quality of therapeutic maneuvers.

Typically, the motion signature will provide a means to determine the quality, quantity and quantitative component elements of the motion as it relates to the desired therapeutic effect. The quality, quantity and quantitative component elements of the motion can be optimized through production of a feedback loop. Thus, the system can include a device, program, or circuitry for producing a feedback loop.

In some embodiments, the systems include at least one wearable sensor and a display. In some embodiments, the system includes at least two wearable sensors and a display. Optionally, the system can include three or more sensors, a sensor network or an array, where at least one sensor is not placed on the patient and the others are placed on the patient. In some embodiments, at least one sensor is placed on the patient at a site suitable for measuring the force on a surface of the patient. Optionally, one or more sensors are placed in another location on the skin or other outer surface of the patient in a location suitable for measuring a change in a biological property, e.g. heat rate, blood flow, breathing depth, temperature and rate.

In some embodiments, the output of the two or more sensors of the system is combined to optimize the therapeutic maneuver that is applied to the subject by the operator in response to quantitation of the motion or the physiological parameters detected by the sensors.

1. CPR

In some embodiments, the systems measure motion and/or other physiological parameters during cardiopulmonary resuscitation (CPR). Techniques for performing CPR on a subject are known in the art and include chest compressions to circulate blood. In some embodiments, the systems include one or more wearable sensors that provide motion signatures of a subject during chest compression. Typically, the systems measure, record and display one or more of angular motion, acceleration, velocity, force or coordinate displacement associated with required repeated compressions of the chest. In some embodiments, the systems record a motion signature on the recipient of CPR. In other embodiments, the motion signatures are recorded from sensors on the operator, device or machine, administering the CPR.

Typically, an optimal CPR motion signature is a signature that produces adequate movement of the subject's blood, leading to revitalization of the subject. Therefore, sensors can monitor any parameter associated with movement of the blood or perfusion or aspects of revitalization such as spontaneous respiration, distal appendage temperature change, limb or body movement, restoration of speech or the like. When an optimal CPR motion signature is recorded, this signature can be used as a guide signature for subsequent CPR on or by the same or different subjects and performed by the same or different operators. For example, a CPR motion signature that is used as a guide CPR motion signature can be used for training operators. In some embodiments, a guide motion signature for CPR can be displayed simultaneously with motion signatures acquired by sensors placed on an operator or a subject during CPR. For example, a guide motion signature for CPR can be displayed by a visual display device as an "overlay" trace superimposed over that of an acquired trace.

CPR and other therapeutic maneuver signatures may be further optimized via collection of a multiplicity of data from multiple subjects, either contemporaneously or over time, creating a community or population of data. These data may be further analyzed via big data, machine algorithms to further identify, define and refine optimal performance signatures. An example of such a use case would occur in a HeartSafe community or the like.

In certain embodiments, the system is used to quantitate and monitor a therapeutic maneuver applied to a subject, such as CPR compression, physiotherapy of a limb, physiotherapy of the torso, physiotherapy of the head and/or neck, ventilation, intubation, or any other manipulation or compression, of a body part.

In certain embodiments, the system is used to quantitate and monitor a therapeutic maneuver applied to a subject, such as CPR compression, physiotherapy of a limb, physiotherapy of the torso, physiotherapy of the head and/or neck, ventilation, intubation, or any other manipulation or compression, of a body part.

In some embodiments, the sensors of the system are adapted to measure, assess, or detect, parameters such as motion (for example, as coordinate displacement in one or more axes), rate of motion (for example, as acceleration and deceleration), force, pressure, angular displacement, velocity, temperature, mass and extension. In an exemplary embodiment, the sensors of the system measure coordinate displacement in more than a single plane, such as two or three different planes. Sensors of the system can measure one or more different parameters simultaneously. In some embodiments, sensors of the system can measure the same or different parameters at different times.

2. Wearable Sensors

Sensors are typically conformal, conformable, or stretchable, sensors that measure parameters such as motion, displacement, acceleration, angular rotation, angular acceleration, compression, pressure, flow, temperature, etc. These sensors are applied topically, to the outside surface of a patient, and/or the medical practitioner , and or the device or system—e.g. Lucas administering force to the patient. The wearable sensors may be in contact with any surface that moves, they may be in contact with an outer surface on a patient. In some embodiments, a sensor is in contact with a surface on the medical practitioner or other person that is applying a force or motion to the patient, e.g. pushing, pulling, or rotating a surface on a patient. In some embodiments, a sensor is in contact with a surface on the machine device or system that is applying a force or motion to the patient, e.g. pushing, pulling, or rotating a surface on a patient. Outer surfaces of the patient to which sensors may be attached include the chest, neck, arm, leg, shoulder, the torso, the digits, the wrist, the back, the buttocks, the groin, the hand, the feet, the tongue, lips, nose or scalp.

Wearable sensors can be worn by a patient, the medical practitioner or other person, or the machine, device or system that is applying a motion to the patient and typically measure data related to one or more motions. Optionally the data in the sensor can be transmitted to other devices, such as smart phones, computers, via Blue tooth, near field or other telecommunication or telemetry means, etc.

Wearable sensors have diagnostic, as well as monitoring applications. Their current capabilities include physiological and biochemical sensing, as well as motion sensing. The sensor may be connected to a battery or to a power source. Optionally, the power source is a mechanical energy harvesting material, which is able to power the sensor via movement of the patient or practitioner applying the force.

Optionally, the sensor contains a piezoelectric material on flexible substrate for energy harvesting, such as described in International Publication No. WO 2015/106282 to The Arizona Board of Regents on Behalf of the University of Arizona and The Board of Trustees of the University of Illinois.

Methods for forming piezoelectric materials on flexible substrates are known. Exemplary methods are described for example in X. Feng, et al., "Stretchable Ferroelectric Nanoribbons with Wavy Configurations on Elastomeric Substrates", ACS Nano, 5 (4): 3326-3332 (2011) and Y. Qi, et al.,"Piezoelectric Ribbons Printed onto Rubber for Flexible Energy Conversion," Nano Lett., 10: 524-528 (2010).

By way of example, if a sensor containing a mechanical energy harvesting material containing PZT ribbons embedded in capacitor type structures generally described below.

A multilayer stack of PZT, a suitable material for the bottom electrode (e.g. PT/Ti,), and silicon dioxide (SiO2) can be coated on a silicon wafer.

PZT ribbons with suitable thicknesses (such as from about 100 nm to about 10 microns) and dimensions may be etched via chemical etching to a hard-baked mask of photoresist.

The top electrode may be formed by depositing a suitable inert, conductive material, such as gold, platinum, or both on the PZT surface of the multilayer stack. The top and bottom electrodes of the PZT ribbon may be defined by photolithography, such as via chemical etching through a hard-baked mask of photoresist.

The resultant ribbons can be protected by a hard-baked photoresist during partial removal of a sacrificial layer underneath the PZT ribbon. In this method the silicon dioxide layer is the sacrificial layer.

The PDMS stamp may be contacted with the ribbon.

Then the multilayered PZT containing devices may be removed from the silicon wafer, such as by peeling them off of the silicon wafer, and placed on a suitable substrate having the desired Young's modulus, typically a high Young's modulus. For example, the multilayered PZT containing devices may be transferred to a PI substrate.

Optionally, the entire device may be coated with an inert, biocompatible material, such as a layer of PI, to protect the sensor.

Contact holes for the top and bottom electrodes are formed, and connection lines for the electrodes are prepared using known methods.

3. Display

The display system includes an LCD display and/or audio system and/or graphical user interface (GUI) and/or wearable headsets, glasses, AR headsets, VR headsets or the like. These are configured to provide one or more of visual, auditory, and tactile output to a medical practitioner or other individual applying motion or other therapeutic maneuvers to a patient.

II. Uses of the Systems to Modify Application of Physical Motion on a Patient.

Therapeutic Uses

In certain embodiments, systems and methods for quantitating the motion and/or physiological parameters of a subject are applied to quantitate and monitor a therapeutic maneuver applied to a subject, such as CPR compression, physiotherapy of a limb, physiotherapy of the torso, physiotherapy of the head and/or neck, ventilation, intubation, or any other manipulation or compression, of a body part.

Optimal placement of sensors is determined according to the site of manipulation or the site most accessible to provide the desired information. Parameters that can be measured include motion, such as coordinate displacement in one or more axes, rate of motion, such as acceleration and deceleration, force, pressure, angular displacement, velocity, temperature, mass and extension. In an exemplary embodiment, coordinate displacement is measured in more than a single plane, such as two or three different planes. Sensors can measure one or more different parameters simultaneously. In some embodiments, sensors measure the same or different parameters at different times.

The sensors are typically wearable sensors, and are placed on the subject according to the site of manipulation or as required by the system. In some embodiments, sensors are placed on the subject to whom a therapeutic maneuver is being applied. In other embodiments, sensors are placed on the operator or machine or system that is performing a therapeutic maneuver on a subject. In other embodiments, sensors are placed on the operator that is performing a therapeutic maneuver on a subject and sensors are placed on the subject to whom a therapeutic maneuver is being applied.

The methods of quantifying sensory information acquired during a therapeutic process can produce an optimized motion signature for the therapeutic process. Typically, the motion signature will provide a means to determine the quality of the motion as it relates to the desired therapeutic effect. The quality of the motion can be optimized through production of a feedback loop. The methods can include reproducing the motion signature of a guide signature. Reproducing can include quantitated motion that is within, for example, an adjustable or preset threshold of less than 20%, 10%, or 5% of the coordinate displacement. For CPR, two thresholds may be used, a first threshold for compression depth, and a second threshold for undesirable lateral displacements of the sternum.

CPR

In some embodiments, the systems and methods measure motion and/or other physiological parameters during cardiopulmonary resuscitation (CPR) techniques. Any techniques for performing CPR on a subject known in the art can be incorporated into the methods. In some embodiments, the methods of using wearable sensors provide a motion signature of a subject during compression of the chest by an operator. Typically, the methods measure, record and display one or more of the angular motion, acceleration, velocity, force or coordinate displacement associated with repeated compression of the chest. In some embodiments, the motion signature can be recorded by sensors on the recipient of CPR. In other embodiments, the motion signature can be recorded by sensors on the operator, system or device administering the CPR.

Typically, an optimal CPR motion signature is a signature that produces adequate movement of the blood, with the goal of revitalization of the subject. Therefore, sensors can monitor any parameter associated with movement of the blood or perfusion or aspects of revitalization such as spontaneous respiration, distal appendage temperature change, limb or body movement, restoration of speech or the like. When an optimal CPR motion signature is recorded, this signature can be used as a guide signature for subsequent CPR on or by the same or different subjects and operators, respectively. For example, a CPR motion signature that is used as a guide CPR motion signature can be used for training operators. In some embodiments, a guide motion signature for CPR can be displayed simultaneously with the motion signature acquired by sensors placed on an operator or a subject during CPR. For example, a guide motion signature for CPR can be displayed by a visual display device as an "overlay" trace superimposed over that of an acquired trace.

Figure 2:
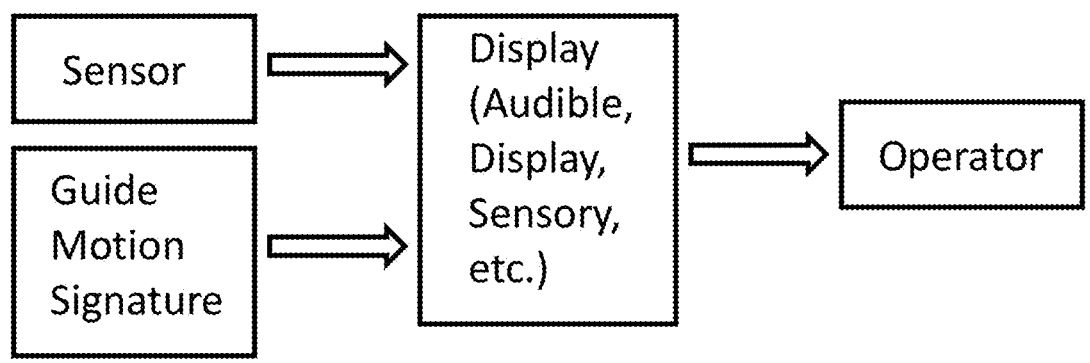
FIG. 2 is a flowchart showing the system of recordation of a motion at a sensor, display of the quantitation of the motion and overlay with a prior-recorded motion signature for comparison.

In some embodiments, the methods of monitoring one or more of the parameters associated with the motion of chest compression during CPR and producing a CPR motion signature are used to guide the process of CPR. An exemplary flow-chart for how systems for monitoring CPR can be used to guide an operator administering CPR is shown in FIG. 2.

Figure 4:
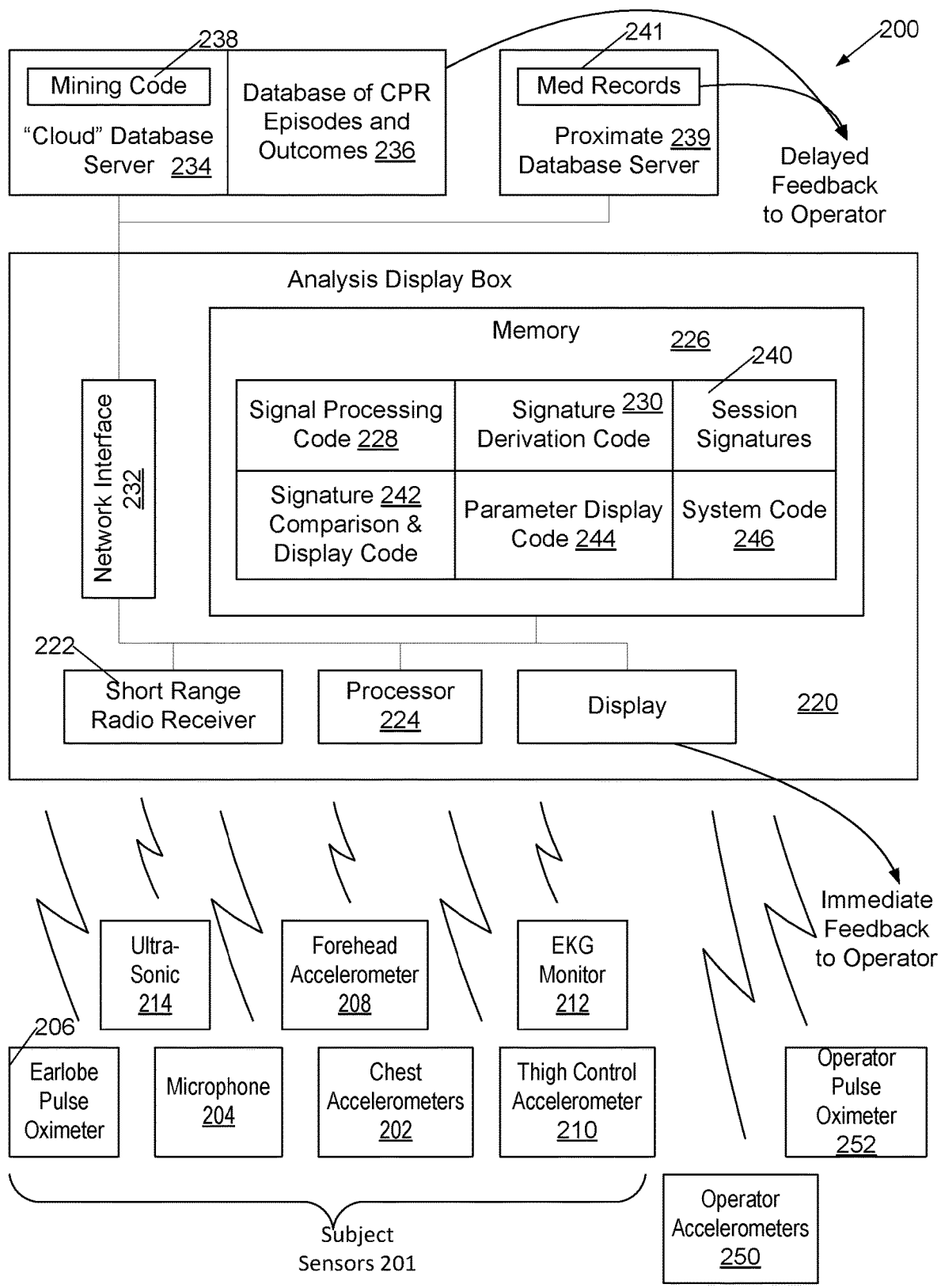
FIG. 4 is a block diagram of a system configured to monitor sensors applied to a subject and/or operator
Figure 5A:
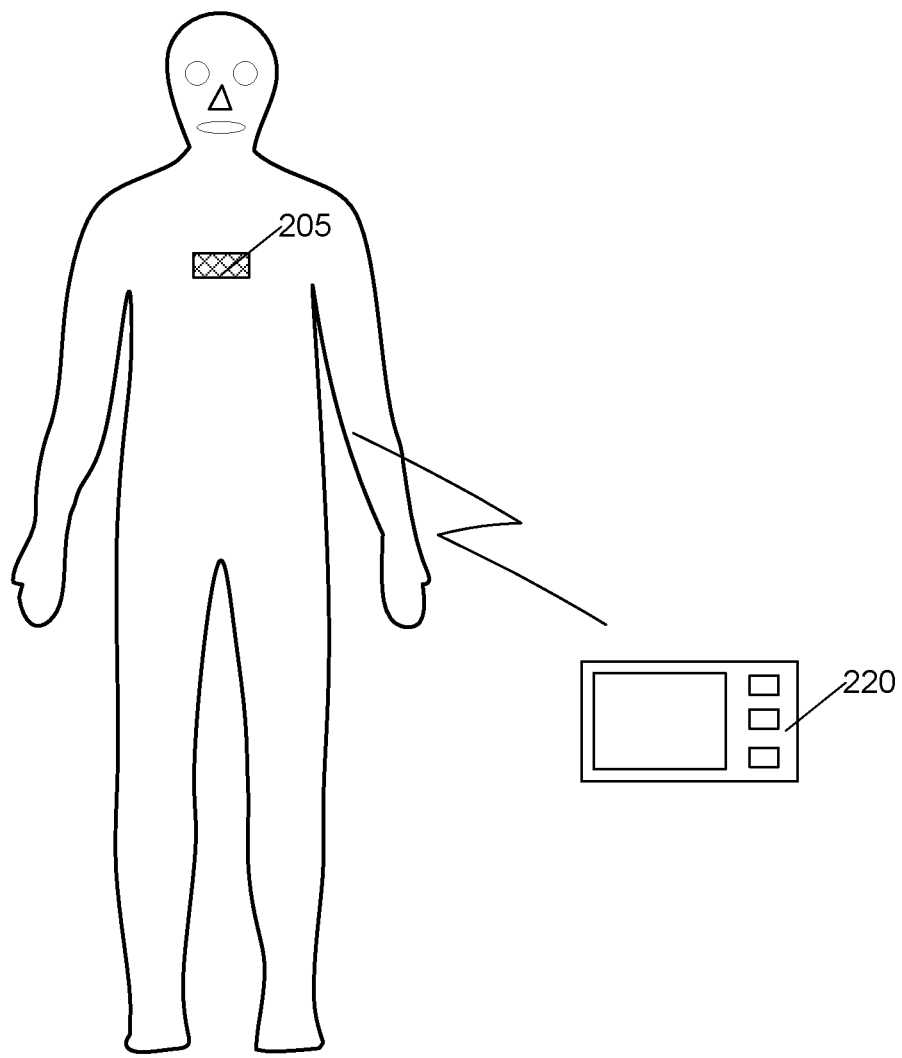
FIGS. 5A and 5B illustrate example sensor locations on a subject.
Figure 5B:
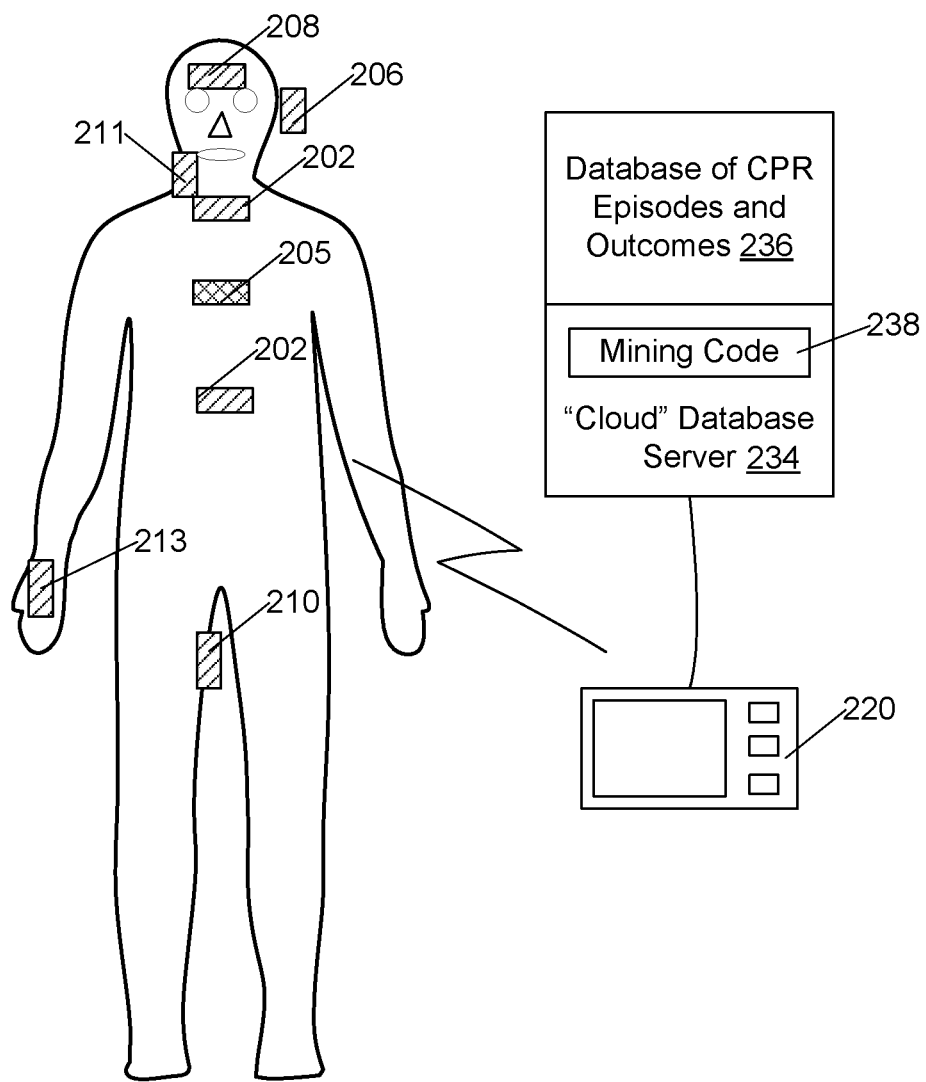

In a particular embodiment, a system 200 for monitoring CPR includes sensors 201 applied to a subject undergoing CPR include, with reference to FIGS. 4-5A and 5B. FIG. 5A shows use of a single sensor 205 with display box 220, and FIG. 5B shows example positions of many sensors 201. Accordingly, any combination of one or more of the sensors 201 may be used:

1) A single chest 3D accelerometer sensor 202 placed at the sternal notch to sense displacement of the chest during therapeutic movement.
2) Two chest 3D accelerometer sensors 202, one placed at the sternal notch, one at the xiphoid process. In an embodiment the 3-D accelerometer at the sternal notch is co-located with a microphone 204 adapted to detect breath sounds in the subject's trachea and lungs. In an alternative embodiment a single center-sternum 3D accelerometer 205 is used. In some embodiments where the center-sternum 3D accelerometer 205 is used, the center-sternum accelerometer is integrated with a force sensor adapted to measure force applied by the operator to the sternum of the subject.
3) An optical blood oxygenation and flow detection device such as a pulse-oximeter 206 clip-on attached to the subject's earlobe.
4) A 3-D accelerometer 208 centered on the subject's forehead.
5) Another 3-D accelerometer 210 and in some embodiments an elastic tension band with monitoring electronics placed on a thigh of the subject to serve as a plethysmographic blood flow detector. In alternative embodiments, in place of thigh plethysmographic sensing, an ultrasonic blood flow sensor is integrated with 3-D accelerometer 210 for placement over the subject's femoral artery or configured to be placed separately 211 over the subject's carotid artery.
6) An electrocardiographic monitor 212, which in a particular embodiment has electrodes integrated with a defibrillator.
7) In some embodiments, a thermometer sensor 213 is placed on a peripheral limb to detect signs of blood flow that alter skin temperature. In some embodiments the 3-D accelerometers are integrated with gyroscopic sensors to measure rotational accelerations as well as linear accelerations.

The 3-D accelerometers and other sensors have a short-range digital radios and batteries, and are linked to an analysis/display box with short-range digital radio links, such as a Bluetooth, Zigbee, or Bluetooth Low-Energy radio.

In an alternative embodiment, instead of applying separate sensors in the aforementioned positions, the sensors are integrated into a flexible sheet, belt, garment or applique, having openings for the subject's mouth and nose or the like, the sheet, belt, garment or applique configured to position the sensors in the aforementioned positions with one or few motions required of a staff member applying the sheet to the subject.

The analysis/display box 220 incorporates a master short-range digital radio transceiver 222 or other telecommunication or telemetry means adapted for operating through the short-range digital radio links other telecommunication or telemetry means to the sensors, a processor 224, and a nonvolatile memory 226 containing signal processing and analysis routines.

In an embodiment, readings of the sternal notch and xiphoid process accelerometers are interpolated by signal processing code 228 to estimate center sternum movement, and the interpolated result is used to estimate compression depth, compression rate, and lateral displacement of the chest while compressions are being performed. In embodiments having central sternal accelerometers, signal processing code 228 need not interpolate, and uses central sternum movements directly to estimate compression depth, compression rate, and lateral displacement of the chest while compressions are being performed.

In a particular embodiment, readings from the 3-D accelerometer 210 located on the subject's thigh are subtracted by signal processing code 228 from readings of the sternal notch and xiphoid process accelerometers prior to estimating compression depth and lateral displacement to compensate for gross movements of the subject such as those encountered in an ambulance rounding corners.

In an embodiment, the forehead 3D accelerometer 208 is used to estimate neck angle, since a head-back position of the neck has been shown to help open a subject's airway to allow air entry during CPR. In a particular embodiment, sounds detected by the microphone 204 at the sternal notch are processed by signal processing code 228 to estimate airflow noise levels; these noises may indicate successful entry of air into the subject's lungs.

The optical blood oxygenation and flow detection pulse-oximeter 206 is read to determine blood oxygenation and determine if blood flow pulsations are detectable, and the electrocardiographic monitor 212 results are processed to indicate whether the subject has a normal heartbeat or has an abnormal cardiac condition such as atrial or ventricular fibrillation, or asystole; the monitor 212 results are also processed to detect applied defibrillator shocks.

In embodiments, subject sensors 201 are configured with protection circuitry to survive administration of shocks from defibrillators, which may be automatic electronic defibrillators (AEDs). In alternative embodiments ultrasonic blood flow sensing devices 214 or a plethysmographic flow detection device integrated with the thigh accelerometer 210, are applied over the subject's carotid or femoral arteries to monitor blood flow, signals from these devices are also processed by analysis and display box 220. In additional alternative embodiments, blood flow sensors are used such as those described in R. C. Webb et al., *Epidermal devices for noninvasive, precise, and continuous mapping of macrovascular and microvascular blood flow*. Sci. Adv. 1, e1500701 (2015), or the like.

One or more of the compression depth, compression rate, lateral displacement, neck angle, airflow rate and noise levels, blood oxygenation and blood flow pulsations, blood flow measurements, and electrocardiographic monitor results are processed into a signature by signature derivation code 230.

Analysis and display box 220 also has a network interface 232 coupled through the Internet to a cloud-based database server 234 having a database of prior CPR episode signatures 236, including outcomes of those episodes, and mining code 238 configured to mine database 236 for characteristics of CPR episodes with successful outcomes. Analysis and display box 220 also has a small database 240 of prior signatures recorded with this analysis and display box and signatures associated with desirable CPR signatures or with well-performed CPR to which a current CPR episode may be compared by signature comparison & display code 242. Also found in memory 226 is operating system code 246 and parameter display code 244.

Many CPR operators are trained with dummies, mannequins or torso facsimiles, often known as "Annies." In a particular embodiment, sensors similar to those applied to a subject, with exception of the electrocardiographic monitor, are built into an Annie and used to generate signatures during training of operators.

Additional information regarding CPR performance can be obtained by instrumenting the CPR operator, or when training with Annies by instrumenting CPR operator trainees.

Additional information regarding CPR performance can be obtained by instrumenting the machine, device or system during automatic or semi-automatic CPR, or when training with Annies by instrumenting CPR machines, devices or systems.

In an embodiment, the operator is instrumented with at least one 3D accelerometer 250 located on his/her hands, forearms, arms, chest, head or torso or shoulders. In a particular embodiment, an additional 3D accelerometer in a sticker is attached to the back of a hand, or to forearms, of the operator. Additionally, the operator may be instrumented with a pulse oximeter 252 worn on the earlobe, or integrated with a 3-D accelerometer worn elsewhere on the body.

The sensors 250, 252 attached to the operator are also linked by short-range digital radio, telemetry or telecommunication means or protocol to the analysis/display box 220. Readings from these sensors are processed to indicate whether the operator is using arms, or body movement from the waist, to perform compressions; to generate a signature of the like and determine via feedback a "best/optimum" signature; and to determine, through sensing the operator's pulse, a peak velocity, rate and depth of compressions, a fatigue level and signature of the operator; operators determined to be fatigued may be relieved with recruitment of additional people or devices. If a sensor is present on the back of the operator's hand, readings from that sensor are processed to determine lateral movements associated with the compressions as well as compression depth, and provide an additional indication of whether the operator is using arms, or body movement from the waist, to perform compressions.

The use of arms or body movement from the waist, operators pulse, lateral movements, compression rate and depth, and operator fatigue indications are also processed by signature derivation code 230 into a signature.

In an embodiment, the analysis and display box also incorporates, within the memory, signature derivation code 230, signature comparison and display code 242, and parameter display code 244. In a first mode of operation, the analysis and display box displays the parameters read from the sensors and produced by processing in processor 224 for the current CPR session. In a second mode of operation, the signature comparison portion of the signature derivation and comparison code displays differences between parameters produced by processing in processor 224 for the current CPR session and parameters associated with a selected signature generated during a prior CPR session. In addition to the short-range digital radio transceiver, telemetry or telecommunication means or protocol adapted for operating through the short-range digital radio links to the sensors, a processor, and a nonvolatile memory containing signal processing and analysis routines, the analysis/display box 220 incorporates in the memory 226 parameters and signatures associated with prior model CPR sessions, some of which may have been obtained during CPR sessions on actual subjects and some of which may have been obtained during training sessions on Annies. The code in memory includes machine readable instructions configured to command the processor to perform the indicated tasks.

Figure 5C:
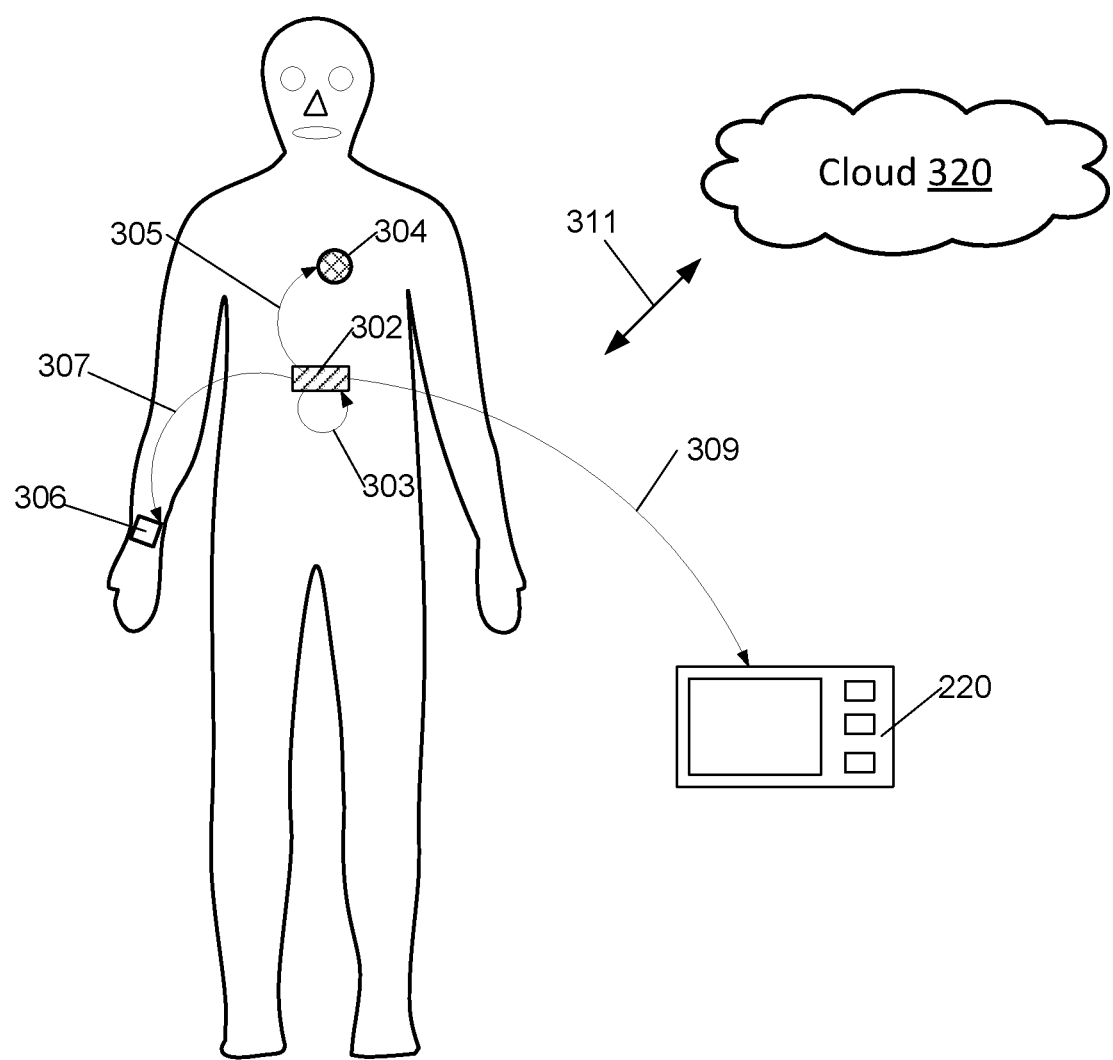
FIG. 5C shows a telemetry system of nested communication loops, in an embodiment.

One embodiment of the system described herein, as shown in FIG. 5C, is a telemetry system of nested communication loops. A first sensor 302 (e.g., one of sensor 201) may sense and store data in internal memory (as indicated by loop 303), the sensor 302 may communicate (as indicated by loop 305) with an implanted device of the subject, such as a fibrillator 304, the sensor 302 may also communicate (as indicated by loop 307) with a wearable device 306 (e.g., a watch, smartphone, or other such device), the sensor 302 may also communicate (as indicated by loop 309) with a free-standing electronic communication device (e.g., analysis and display box 220), each of which may in turn communicate with the cloud 320 (e.g., the World wide web). In certain embodiments, all these devices may communicate with each other, or in specific hierarchies.

Figure 6:
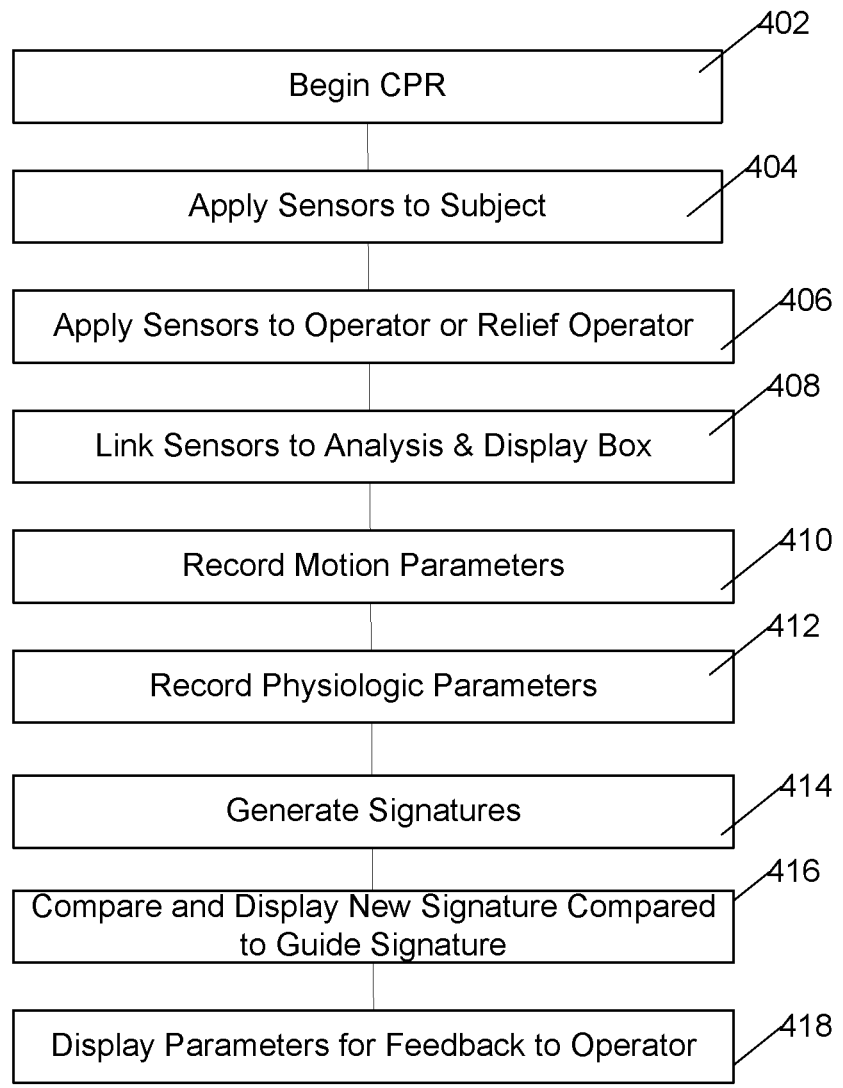
FIG. 6 is a flowchart of the method of using the sensor systems to monitor CPR.

A method of performing CPR using the system described herein is illustrated in the flowchart of FIG. 6.

Since delays in initiation of CPR can be fatal, CPR is begun 402 by the first rescuer on scene, who also activates alarms and summons additional support such as a crash cart bearing a defibrillator, or a team or ambulance crew with portable defibrillator, advanced cardiac life support medications, and the system described herein.

After arrival of the system, the methods include the steps of applying 404 the one or more sensors to the subject, the operator/device 406 or both the subject and the operator/device. Exemplary sensors are wearable sensors as described herein. In some embodiments, the sensors are BIOSMART® (trademark of MC10, inc. Lexington, Mass.) wearable sensors or the like. The sensors are linked 408, preferably wirelessly, to one or more devices for recording and displaying the measured parameter(s) like analysis and display box 220. The methods include recording 410 motion parameters during the CPR. In some embodiments, the methods include a step of recording 412 one or more physiological parameters, such as blood oxygenation or blood flow, or temperature during CPR. In some embodiments, the methods include the step of generating 414 a CPR signature. In some embodiments, the methods include the step of displaying 416 the CPR signature relative to a guide or reference CPR motion (or other parameter) signature. The methods can optionally include the step of monitoring one or more of the measured parameters 418 during CPR relative to one or more guide parameters. The guide parameters can be used to provide feedback to the operator, for example, to establish the efficacy of the CPR technique being applied.

Figure 3:
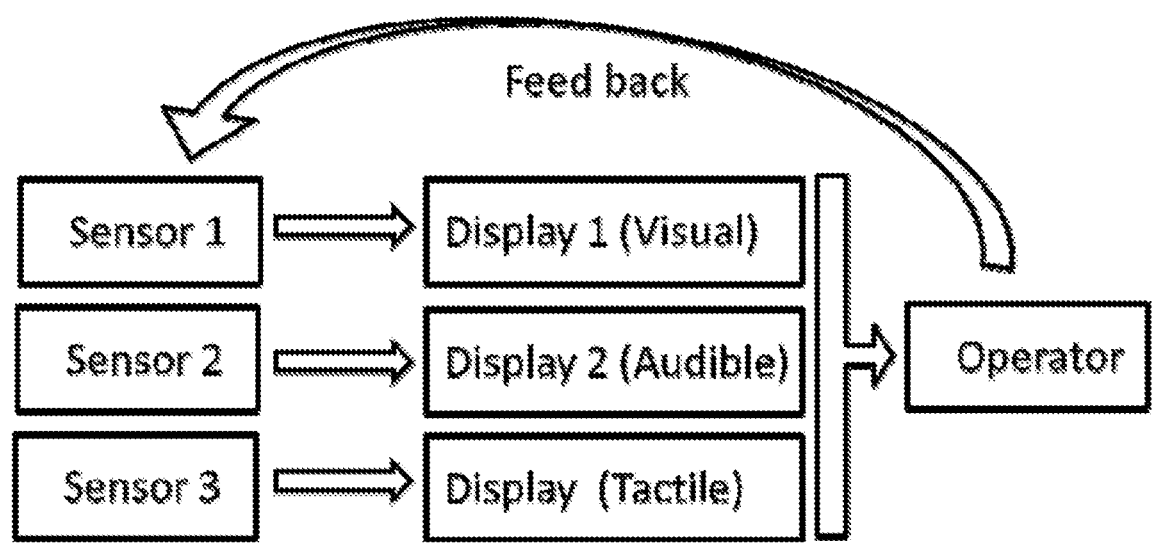
FIG. 3 is a flowchart showing the system of recordation of a motion at a sensor, display of the quantitation of the motion and feedback to the operator applying the motion.

Exemplary guide parameters include a guide motion signature, or any parameter indicative of effective perfusion or revitalization of the subject. In some embodiments, the guide parameter is the body temperature of the subject. For example, an increase in skin temperature of the subject receiving CPR can be indicative of restoration of blood within the subject. Therefore, in some embodiments, the methods include monitoring skin temperature of limbs of the subject during CPR. Other guide parameters include pressure, for example, pressure associated with the pulse of blood within the subject. Therefore, in some embodiments, motion or other parameters associated with the pulse are used as a guide for CPR. When one or more CPR guide signatures and/or other guide parameters are used, the methods can include monitoring the multiple guides and the motion signature generated by the CPR in a closed-loop fashion to produce an optimized CPR motion signature. Typically, CPR performed on the subject according to the optimized CPR motion signature provides an enhanced therapeutic effect in the subject relative to CPR performed in the absence of the optimized CPR motion signature. An exemplary method of preforming CPR on a subject using three sensors in a closed-loop feedback circuit to produce an optimized CPR motion signature is provided in FIG. 3. FIG. 3 is a flow-chart demonstrating the use of sensory input from three sensors providing three different output signals (visual, audio and tactile), such as a graphical display, an audible alarm, and a vibrating alarm, for example, embedded in a wearable device worn by the operator. The operator can vary the parameters of CPR (e.g., force, regularity and continuity of compression, spacing between breaths given, etc.) according to the parameters displayed by one or more the display systems, to achieve optimal perfusion of the subject without unduly exhausting the operators.

Mechanically Assisted CPR

There have been systems marketed that provide mechanical assistance for CPR; these system may provide chest compression, ventilation timed between compressions, oxygen, heartbeat monitoring, and similar assistance to operators performing CPR.

The system of FIGS. 4 and 5 is compatible with and may be used in conjunction with mechanical CPR support systems such as Lucas or Thumper—see http://www.lucas-cpr.com/en/lucas_cpr/lucas_cpr; https://www.ems1.com/ems-products/Mobile-Data/articles/233994048-Automated-chest-compression-devices-10-things-you-need-to-know-to-save-lives/ and https://en.wikipedia.org/wiki/AutoPulse. The system of FIGS. 4 and 5 may be integrated with mechanical CPR support systems. Mechanical CPR support systems may also be adapted to use data, such as blood flow and oxygenation data, from the system of FIGS. 4 and 5 for immediate feedback to adjust rate, depth, and other characteristics of mechanical CPR provided to a subject.

Telemetry and Data Mining

As noted above, the system with reference to FIGS. 4 and 5 can give immediate feedback to an operator to improve CPR performance by comparison of signatures from the present CPR session with desirable CPR guideline signatures, whether sensors are worn by the subject, by the operator, or both.

As noted with reference to FIGS. 4 and 5, a function of analysis/display box 220 is to record data derived from sensor readings, which may be referred to as telemetry data and which may be in the form of generated signatures, in a local database in memory 226 as a CPR episode unfolds. This data may in embodiments be forwarded to a proximate database server 239 for entry in a database 241, such as hospital or ambulance company databases, where it may be entered into a patient record associated with the subject, and may also be compared with desirable CPR signatures and otherwise analyzed to provide delayed feedback to operators. This data may also be forwarded to a network-based "cloud" server 234 for entry into a large database 236 of CPR session signatures, together with an outcome of the CPR session and other information regarding the subject, where it may be mined for correlations between the signatures recorded during the session, outcome, patient data including medications used before or during the CPR session, and other information that may lead to improvement of CPR procedures.

Figure 7:
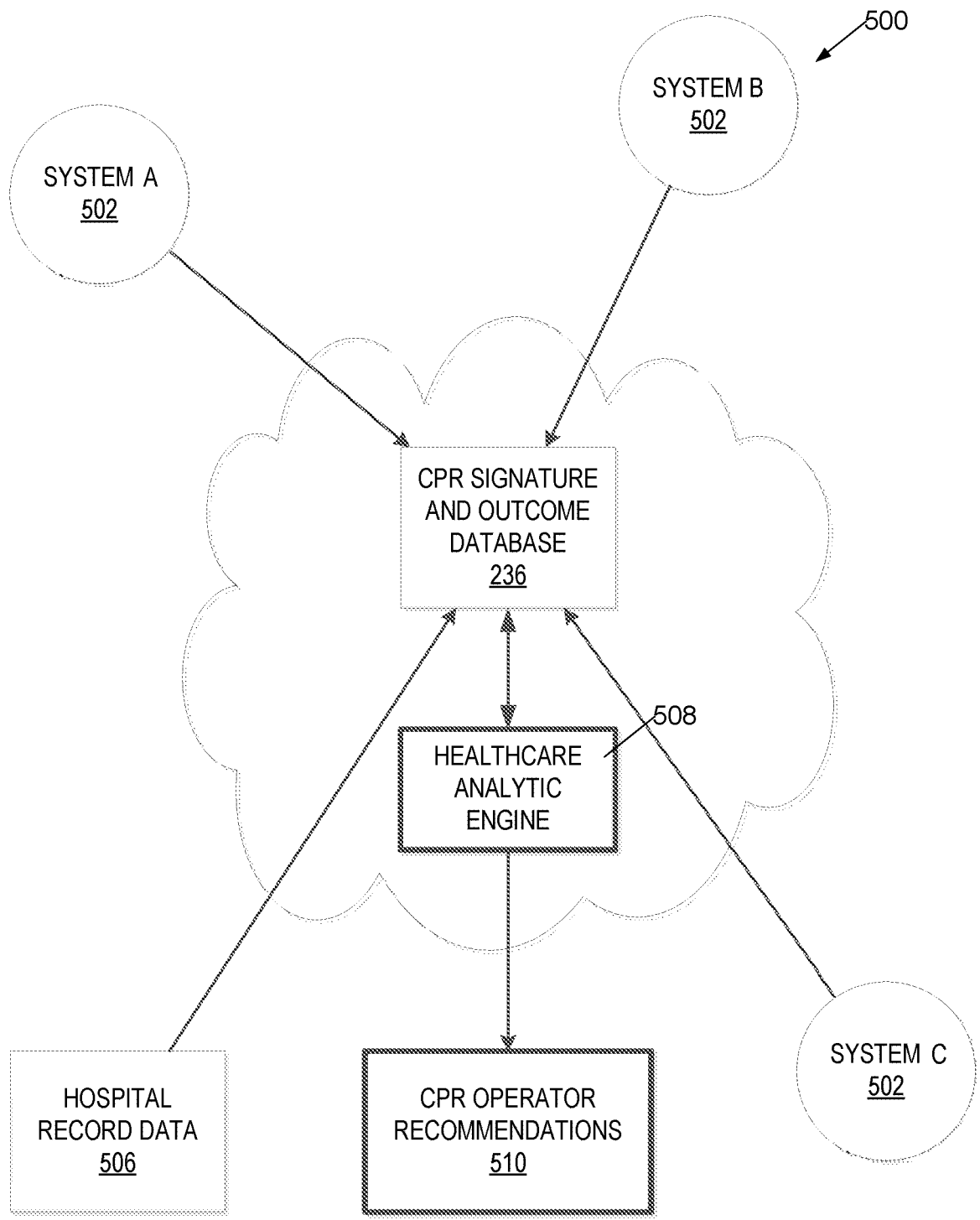
FIG. 7 is a block diagram illustrating data storage associated with the system and opportunities for data mining to improve recommended procedures for operators.

In an embodiment 500, cloud server 234 is in communication with multiple systems 502 (FIG. 7) each corresponding to a system as illustrated in FIGS. 4 and 5, located in potentially many hospitals and/or external to a hospital, i. e. in the community where an out-of hospital CPR event has occurred, with information sourced from a wired patient regardless of location. Each time a CPR event completes, signature data associated with that event is uploaded by systems 502 to the CPR signature event and outcome database 236, and each associated hospital, ambulance company 506 or other information source or sensors from a CPR event, regardless of location, telemetry or telecommunication means or protocol, uploads information from patient records associated with subjects of CPR that are even potentially of interest to analysis of CPR events such as but not limited to medications, such as epinephrine, that may have been administered during CPR, internal or external defibrillator makes, models, and settings used during the event, diagnoses associated with relevant or contemporary illnesses of the subject such as but not limited to asthma, pneumonia, and cardiovascular disease including treatment given for those conditions, pacemakers implanted in the subject and their settings, pathology and laboratory reports, and other potentially relevant information. In a particular embodiment, subject's entire medical histories and records are inserted into database 236. Data mining or healthcare analytic engine 508 may then analyze information from multiple CPR episodes in database 236 to identify characteristics of successful and unsuccessful resuscitations to provide recommendations 510 for improvements in CPR procedures, thereby providing another source of delayed, but potentially important, feedback to operators, equipment and drug manufacturers, those who formulate CPR recommendations, the FDA, and others in the medical care industry.

The methods can be employed in the training of operators or machines by providing immediate feedback, as well as in the application of CPR to subjects in need thereof.

Analysis of signatures in hospital records in proximate medical record database 241 may also provide delayed feedback for improving operator performance.

The present invention will be further understood by reference to the following non-limiting examples.

EXAMPLES

Example 1. Application of CPR by Different Medical Professionals and Less Trainer Volunteers Materials and Methods CPR was carried out on the same test subject by each of nine different operators with differing degrees of experience in administering CPR. A flexible BIOSTAMP® (trademark of MC10, inc. Lexington, Mass.) wearable sensor was fitted to the test subject's chest to monitor the motion of CPR at site of application.

CPR was applied for a fixed amount of time by each operator. CPR was applied according to the preferred technique of each of the nine operators. During CPR the motion and force at the site of the wearable sensor was monitored as acceleration in each of three directions (X,Y,Z) over time (seconds). Measurement of the motion during CPR applied by each of the nine operators was recorded and displayed in graphical format on a visual display.

Results

Exemplary graphs quantitating the compression (acceleration) of the chest measured over the same time course during CPR by five of the operators are shown in each of FIGS. 1A-1E, respectively. In FIG. 1A, a top line 102 represents accelerations in Z axis, while lower lines 104 and 106 represent lateral accelerations in X and Y axes. We note that accelerations in Z axis are required for chest compression, but accelerations in X and Y axes represent lateral motions that may fracture ribs and typically do not contribute to chest compression.

FIGS. 1A-1E demonstrate that acceleration in each of planes X, Y, and Z vary significantly in the degree of coordinate displacement effectuated by the motion associated with compression. The quantitation of effectuated motion represents the CPR "motion signature" for each of the operators, respectively.

A comparison of the CPR motion signatures depicted in FIGS. 1A and 1C, respectively, are those produced by operators experienced in effective CPR technique. These motion signatures show regularly-spacing and coordinate displacement in each of the three planes measured.

The CPR motion signatures depicted in FIGS. 1B, 1D and 1E are produced by less-experienced operators. These motion signatures show irregular spacing and varied coordinate displacement in each of the three planes measured throughout the procedure. These motion signatures betray poor actual CPR performance while the operators involved may have believed they were providing good CPR performance.

Unless defined otherwise, all technical and scientific terms used herein have the same meanings as commonly understood by one of skill in the art to which the disclosed invention belongs. Publications cited herein and the materials for which they are cited are specifically incorporated by reference.

Combinations

The features described herein can be implemented in an assortment of combinations. Among these are:

A system designated A adapted to monitor cardiopulmonary resuscitation (CPR), including at least one three-dimensional (3D) accelerometer, the 3D accelerometer selected from a 3D accelerometer configured for attachment to a center of a sternum of a subject and a pair of 3D accelerometers including a 3D accelerometer configured for attachment over a sternal notch of a subject and a 3D accelerometer configured for attachment over a xiphoid process of the subject, the 3D accelerometers comprising a digital radio adapted to link to a master short range digital radio. The system also includes an analysis and display unit including the master short-range digital radio, telemetry or telecommunications means, a processor, a memory, a signature database stored within the memory further comprising at least one signature corresponding to a prior CPR session, and code including machine readable instructions configured to direct the processor to read accelerometer data through the short range digital radio from the accelerometers, to determine vertical and lateral movements of the subject's chest from the accelerometer data, and to determine and display parameters derived from the movements of the subject's chest including depth and rate of CPR compressions, and to compare a signature derived from a present CPR session to the at least one signature corresponding to a prior or ideal CPR session.

A system designated AA including the system designated A and including at least one physiologic sensor, the at least one physiologic sensor including an optical oxygen saturation and pulse detection device, and wherein the code includes machine readable instructions to display determined oxygen saturation and detected pulse.

A system designated AB including the system designated A or AA further including an electrocardiographic sensor and wherein the code includes machine readable instructions to indicate on the display whether the subject has a normal heartbeat or has an abnormal cardiac condition.

A system designated AC including the system designated A, AA, or AB further including a microphone, and wherein the code includes machine readable instructions to determine presence of airflow from data received from the microphone.

A system designated AD including the system designated A, AA, AB, or AC wherein at least one accelerometer is configured with gyroscopic sensors.

A system designated AE including the system designated A, AA, AB, AC, or AD wherein the sensors further comprise sensors comprising accelerometers configured for attachment to an operator performing CPR, and the analysis and display unit is configured to determine an extent of the operator's use of arm muscles to perform compressions.

A system designated AF including the system designated A, AA, AB, AC, AD or AE wherein the sensors further comprise an ultrasonic flow detection sensor adapted for placement over a carotid or femoral artery of the subject.

A system designated AG including the system designated A, AA, AB, AC, AD, AE or AF wherein the analysis and display unit further comprises code for communicating signatures of CPR sessions to a database server.

A method designated B of monitoring cardiopulmonary resuscitation (CPR), including
receiving, over a short range digital radio link, sensor data including accelerometer data from at least one three-dimensional accelerometer configured for attachment to a subject, the accelerometer data indicative of accelerations of a sternum of the subject; and determining vertical and lateral movements of the subject's chest from the accelerometer data, and
displaying parameters derived from the movements of the subject's chest including depth and rate of CPR compressions and lateral motions.

A method designated BA including the method designated B further including determining a motion signature and comparing the motion signature to desirable motion signatures.

A method designated BB including the method designated B or BA wherein the parameters are displayed in real time as feedback to an operator to assist the operator to perform more effective CPR.

A method designated BC including the method designated B, BA, or BB wherein the sensor data includes data from a bloodflow sensor and the parameters displayed further comprise a measure of blood flow.

A method designated BD including the method designated B, BA, BB, or BC wherein the sensor data includes data from a pulse oximeter sensor and the parameters displayed further comprise blood oxygenation.

A system designated C adapted to monitor therapeutic movements or manipulations including cardiopulmonary resuscitation (CPR), including at least one sensor for measuring one or more of displacement, force, and movement of a subject's chest, an analysis and display unit having a processor and a memory storing machine readable instructions configured to direct the processor to: read the at least one sensor; determine vertical and lateral movements of the subject's chest; determine and display parameters derived from the movements of the subject's chest including depth and rate of CPR compressions.

A system designated CA including the method designated C, the sensor including a three-dimensional (3D) accelerometer selected from the group consisting of a 3D accelerometer configured for attachment to a center of a sternum of a subject and a pair of 3D accelerometers including a 3D accelerometer configured for attachment over a sternal notch of a subject, and a 3D accelerometer configured for attachment over a xiphoid process of the subject.

A system designated CB, including the system designated C or CA, the sensor further comprising a digital radio adapted to link to a master short range digital radio of the analysis and display unit.

A system designated CC, including the system designated C, CA or CB, the parameters comprising one or more of dimensions, velocity, acceleration, rotation, frequency, regularity, periodicity, intensity, pressure of movement, pressure generated by movement, and shear of movement.

A system designated CD, including the system designated C, CA, CB or CC, further including a signature database stored within the memory and including at least one signature corresponding to a prior or ideal CPR session, the memory further comprising machine readable instructions configured to direct the processor to compare a signature derived from a present CPR session to the at least one signature corresponding to a prior or guideline CPR session to provide immediate feedback to a CPR operator.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A system adapted to monitor chest compressions of cardiopulmonary resuscitation (CPR), comprising:
   at least one sensor adapted to be coupled to a subject's chest and configured for measuring one or more of displacement, velocity, acceleration, rotation, and applied force;
   an analysis, storage, and display unit having a processor and a memory storing machine readable instructions configured to direct the processor to:
   read the at least one sensor;
   determine parameters derived from readings of the at least one sensor; and
   display the parameters derived from the readings of the at least one sensor, the parameters including measurements of vertical depth of CPR compressions, rate of CPR compression, and lateral movements of the subject's chest.

2. The system of claim 1 wherein the at least one sensor comprises a microphone and the parameters further include breath rate and depth of the subject.

3. The system of claim 2, further comprising a telemetry system of nested loops wherein the sensor communicates with one or more of an implanted device of the subject, a wearable device, a free-standing electronic communication device, and a server accessible over the internet.

4. The system of claim 2, the sensor comprising a three-dimensional (3D) accelerometer selected from the group consisting of a 3D accelerometer configured for attachment to a center of a sternum of a subject and a pair of 3D accelerometers including a 3D accelerometer configured for attachment over a sternal notch of a subject, and a 3D accelerometer configured for attachment over a xiphoid process of the subject.

5. The system of claim 4, at least one of the at least one sensor further comprising a short range digital radio adapted to link to a short range digital radio of the analysis and display unit.

6. The system of claim 5, the parameters comprising one or more of dimensions, velocity, acceleration, rotation, frequency, regularity, periodicity, intensity, pressure of movement, pressure generated by movement, and shear of movement.

7. The system of claim 6, further comprising a signature database stored within the memory and including at least one signature corresponding to a prior or ideal CPR session, the memory further comprising machine readable instructions configured to direct the processor to compare a signature derived from a present CPR session to the at least one signature corresponding to a prior or guideline CPR session to provide immediate feedback to a CPR operator.

8. The system of claim 7, further comprising a microphone, and wherein the code includes machine readable instructions to determine presence of airflow from data received from the microphone.

9. The system of claim 7, the at least one sensor further comprising gyroscopic sensors.

10. The system of claim 7, wherein the sensors further comprise sensors comprising accelerometers configured for attachment to an operator performing CPR, and the analysis and display unit is configured to determine an extent of the operator's use of arm muscles or other musculature to perform compressions.

11. The system of claim 7, wherein the sensor comprises an array of sensors configured with a garment.

12. The system of claim 7, further comprising at least one physiologic sensor, the at least one physiologic sensor including one or more of an optical oxygen saturation sensor, a pulse detection device, and a temperature measuring device, and wherein the code includes machine readable instructions to display one or more of determined oxygen saturation, detected pulse or perfusion, and rewarming.

13. The system of claim 12, wherein the sensors further comprise a flow detection sensor adapted for placement over the point of maximum intensity (Cardiac PMI) and/or a carotid, femoral or other arterial pulse point of the subject.

14. The system of claim 12, wherein the analysis and display unit further comprises code for communicating signatures of CPR sessions to a database server.

15. The system of claim 12, further comprising an electrocardiographic sensor and wherein the code includes machine readable instructions to indicate on the display whether the subject has a normal ECG or configuration pattern or has an abnormal cardiac condition.

16. The system of claim 15, further comprising a microphone, wherein the code includes machine readable instructions to determine presence of airflow in the subject's chest from data received from the microphone.

17. The system of claim 16, wherein the sensors further comprise sensors comprising accelerometers configured for attachment to an operator performing CPR and linked by short range digital radio to the analysis and display unit, and the analysis and display unit is configured to determine an extent of the operator's use of hand, forearm, arm, and torso muscles to perform compressions.

18. The system of claim 17, wherein the sensors further comprise a blood flow detection sensor adapted for placement over one of a point of maximum intensity (Cardiac PMI), a carotid, femoral or other arterial pulse point of the subject.

19. The system of claim 18, wherein the analysis and display unit further comprises code for uploading the signature derived from a present CPR session to a database server for entry into a database.

20. The system of claim 19, further comprising data-mining code configured to identify characteristics of successful and unsuccessful resuscitations by analyzing a plurality of signatures stored in the database.

21. The system of claim 18, the flow detection sensor being selected from the group consisting of ultrasonic, plethysmographic, optical, and temperature sensors.

22. A method of monitoring cardiopulmonary resuscitation (CPR), comprising:
receiving, over a short range digital radio, sensor data including accelerometer data from at least one three-dimensional accelerometer configured for attachment to a subject, the accelerometer data indicative of accelerations of a sternum of the subject; and
determining vertical and lateral movements of the sternum from the accelerometer data, and displaying parameters derived from the movements of the sternum including depth and rate of CPR compressions and lateral motions.

23. The method of claim 22, further comprising determining a motion signature from the sensor data and comparing the motion signature to desirable motion signatures of CPR.

24. The method of claim 23, wherein the sensor data includes data from a bloodflow sensor and the parameters displayed further comprise a measure of blood flow.

25. The method of claim 23, wherein the sensor data includes data from a pulse oximeter sensor and the parameters displayed further comprise blood oxygenation.

26. The method of claim 22, wherein the parameters are displayed in real time as feedback to an operator to assist the operator to perform more effective CPR.

* * * * *